United States Patent
Armbruster et al.

(10) Patent No.: US 6,849,579 B2
(45) Date of Patent: Feb. 1, 2005

(54) SYNERGISTIC QUINCLORAC HERBICIDAL COMPOSITIONS

(75) Inventors: James A. Armbruster, Kansas City, MO (US); Dale R. Sanson, Kearney, MO (US)

(73) Assignee: PBI Gordon Corporation, Kansas City, MO (US)

( * ) Notice: Subject to any disclaimer, the term of this patent is extended or adjusted under 35 U.S.C. 154(b) by 30 days.

(21) Appl. No.: 10/603,956

(22) Filed: Jun. 25, 2003

(65) Prior Publication Data

US 2004/0266623 A1 Dec. 30, 2004

(51) Int. Cl.[7] ..................... A01N 43/42; A01N 43/653; A01N 43/56; A01N 43/84; A01N 43/824
(52) U.S. Cl. .................. 504/130; 504/139; 504/225; 504/247; 504/263; 504/273; 504/282; 504/352
(58) Field of Search .................. 504/130, 139, 504/225, 247, 263, 273, 282, 352

(56) References Cited

U.S. PATENT DOCUMENTS

| | | | | |
|---|---|---|---|---|
| 4,971,630 A | 11/1990 | Skaptason | .................. | 37/38 |
| 5,196,044 A | 3/1993 | Caulder et al. | ................ | 57/12 |
| 5,688,971 A | 11/1997 | Kwiatkowski et al. | | |
| 5,700,759 A | 12/1997 | Caulder et al. | .................. | 37/2 |
| 5,877,117 A * | 3/1999 | Anderson et al. | ........... | 504/130 |
| 6,013,605 A | 1/2000 | Rees et al. | ..................... | 43/90 |
| 6,034,034 A | 3/2000 | Caulder et al. | ................... | 37/2 |
| 6,117,823 A | 9/2000 | Smiley | ......................... | 37/12 |
| 6,239,293 B1 | 5/2001 | Liu | .............. | 493/14 |
| 6,307,129 B1 | 10/2001 | Ward et al. | ..................... | 5/10 |
| 6,323,153 B1 | 11/2001 | Smiley | | |
| 6,323,156 B1 | 11/2001 | Smiley | | |
| 6,503,869 B1 | 1/2003 | Beste et al. | ...................... | 37/2 |
| 6,689,719 B2 * | 2/2004 | Jimoh | ........................ | 504/128 |

FOREIGN PATENT DOCUMENTS

EP          1128729          9/2001

* cited by examiner

*Primary Examiner*—S. Mark Clardy
(74) *Attorney, Agent, or Firm*—Hovey Williams LLP

(57) ABSTRACT

A selective synergistic postemergent herbicide composition is provided for the control of undesired broadleaf vegetation and grassyweeds comprising the combination of quinclorac and a selective herbicidal protox inhibitor. About 0.05 part to about 0.1 part by weight of the protox inhibitor is provided for each part by weight of quinclorac. Better synergistic results are obtained from the combination of quinclorac, a selective herbicidal protox inhibitor, and a selective herbicidal auxinic agent. About 0.05 part to about 0.1 part by weight of the protox inhibitor is provided for each part by weight of quinclorac, and about 1 part to about 4 parts by weight of the auxinic herbicidal agent for each part by weight of quinclorac. The synergistic composition hereof has been found to provide more rapid and better control of grassy weeds such as crabgrass than presently registered herbicides.

58 Claims, No Drawings

SYNERGISTIC QUINCLORAC HERBICIDAL COMPOSITIONS

FIELD OF THE INVENTION

The present invention relates to a selective synergistic postemergent herbicidal composition for the control of undesired vegetation when applied to the locus of the vegetation. Quinclorac, 3,7-dichloro-8-quinolinecarboxylic acid (CAS 84087-014), certain protoporphyrinogen oxidase inhibitors, herein referred to as "protox inhibitors," and a number of herbicidal auxinic agents have been used individually for selective control of noxious weeds and plants without significant damage to desirable grasses and the like. Heretofore, it had not been recognized that when quinclorac is combined with a protox inhibitor or a protox inhibitor plus herbicidal auxinic compound in certain relative proportions, the combination exhibits an unexpected synergistic herbicidal effect providing more effective control of difficult to eradicate grassy weeds and undesirable broadleaf vegetation than the individual herbicidal materials used alone at comparable application rates.

Protox inhibitors that exhibit herbicidal synergistic effects in combination with quinclorac include carfentrazone-ethyl (CAS 128639-02-1), sulfentrazone (CAS 122836-35-5), and pyraflufen-ethyl, 2-chloro-5-(4-chloro-5-difluoromethoxy-1-methylpyrazol-3-yl)-4-fluorophenoxyacetic acid ester (CAS 129630-17-7). Protox inhibitors has been found to synergize the herbicidal effectiveness of a number of herbicidal auxinic agents including herbicidally active phenoxy, benzoic, pyridine, quinolinecarboxylic acid compounds, other than quinclorac, and amine and inorganic salts thereof.

BACKGROUND OF THE INVENTION

Herbicidal auxenic compounds have been used for many years to control broadleaf noxious weeds without damage to desirable grasses infested with the weeds. 2,4-D, 2,4-DP, 2,4-DB, MCPP, MCPA, MCPB, which are exemplary herbicidal auxinic compounds, have all been registered and long used individually or in combination as herbicides for treating turf to control undesirable broadleaf vegetation without significantly adversely affecting desirable grasses. Similarly, herbicidal protox inhibitors such as carfentrazone-ethyl, sulfentrazone, and pyraflufen-ethyl have in recent years been used to control undesirable broadleaf vegetation. Although auxinic and protox inhibitor compounds as described have individually been found to be effective in broadleaf weed control without significant damage to desirable grasses, these compounds have not been known to be effective for control of grassy weeds, such as crabgrass, goosegrass and dahlisgrass.

Thus, there continues to be a need for increasing the herbicidal effectiveness of exemplary herbicidal protox inhibitors and herbicidal auxinic compounds, which have heretofore been used alone or in combination, and especially to provide a herbicidal composition that will not only control noxious broadleaf vegetation, but also be effective against grassy weeds without adversely effecting desirable grasses. The urgency of the need is exacerbated by increasing governmental oversight of the sale and approved use rate of herbicidal materials. The recommended level of herbicide that may be applied per unit of area is under pressure from governmental, as well as for economic and environmental reasons.

In addition, certain species of undesirable broad leaf vegetation and grassy weeds are becoming more and more resistant to a number of the most widely used herbicides. Thus, on one hand ever more stringent conditions are being placed on the type and use rate of herbicides, while on the other hand accepted herbicides are becoming less and less effective over time in certain species of noxious weeds.

Furthermore, it is very expensive and time consuming to seek and obtain registration of a new herbicidal compound, including its proposed use rate. Approval data required must not only include evidence of efficacy at the application rates proposed but also the safety of the herbicide when applied at the recommended level.

Accordingly, demonstration of synergism by the combination of existing herbicidal agents, permits use of the individual components of the synergistic combination at lower rates than when used alone, and in many instances ameliorates increasing resistance to herbicidal effectiveness.

Accordingly, there is a great need for improved broadleaf and grassy weed control compositions and a method of controlling such noxious vegetation without adversely affecting desirable plants and which reduces the amount of chemical herbicidal agent necessary to obtain the acceptable weed control.

BRIEF SUMMARY OF THE INVENTION

This invention relates to the discovery that when quinclorac, a herbicidal protox inhibitor and a herbicidal auxinic agent are combined, the resulting combination exhibits synergistic herbicidal effects, which are equal to or better than the herbicidal efficacy of the individual herbicides, even though each of the constituents is present at a lower concentration than the required amount of each herbicide applied alone.

In particular, tests have shown that when quinclorac, a herbicidal protox inhibitor and an auxinic herbicide agent are combined, and the resulting composition is applied at a recommended application rate for control of undesired broadleaf vegetation and grassy weeds, a demonstrable synergistic effect is obtained. It has unexpectedly been found that when a protox inhibitor is combined with quinclorac, the combination containing a lesser amount of quinclorac than recommended as a single herbicidal agent, not only exhibits more effective control of broadleaf weeds, but in addition this combination provides better control of grassyweeds than when quinclorac is applied alone, all without significant damage to desirable turf and grasses. This synergistic effect in controlling broadleaf noxious vegetation as well as grassy weeds is enhanced even more by the addition of an auxinic compound.

The selective synergistic postemergent herbicidal composition for the control of undesired vegetation when applied at a recommended application rate to the locus of undesired vegetation includes from about 0.1 to about 1 lb/acre of quinclorac and from about 0.005 to about 0.06 lb/acre of a selective protox herbicidal inhibitor. Better results are obtained when the amount of quinclorac is supplied at a rate of about 0.18 to about 0.75 lb/acre and a sufficient amount of the protox inhibitor is provided at a rate of about 0.01 to about 0.05 lb/acre. Best results are obtained when a sufficient amount of quinclorac is provided to supply about 0.375 lb/acre of quinclorac.

Similarly, better results are obtained when the amount of the protox inhibitor is sufficient to supply from about 0.01 to about 0.05 lb/acre, and best results are obtained when the protox inhibitor provided is sufficient to supply from about 0.02 to about 0.03 lb/acre.

Synergistic results are preferably obtained by providing a sufficient amount of the active herbicidal ingredients to supply from about 0.1 to about 1 lb/acre of quinclorac, from about 0.005 to about 0.06 lb/acre of the protox inhibitor and from about 0.15 to about 2 lbs/acre of the auxinic compound.

Improved synergism is obtained between the quinclorac, the protox inhibitor and the auxinic herbicide agent when a sufficient amount of the active ingredients is provided to supply from about 0.18 to about 0.75 lb/acre of quinclorac, from about 0.01 to about 0.05 lb/acre of the protox inhibitor, and from about 0.25 to about 1.5 lbs/acre of the auxinic herbicide. Best synergistic results obtain by combining sufficient quinclorac, protox inhibitor and auxinic herbicide when the composition contains an amount of the active ingredients to provide about 0.375 lb/acre of the quinclorac, from about 0.02 to about 0.03 lb/acre of the protox inhibitor, and about 0.75 lb/acre of the auxinic herbicide.

Exemplary protox inhibitors useful in the present invention include carfentrazone-ethyl, sulfentrazone, pyraflufen-ethyl, flumiclorac-pentyl, flumioxazin, fluthiacet-methyl, aclonifen, bifenox, chlomitrophen, ethoxyfen, fluoroglycofen-ethyl, fomesafen, lactofen, oxyfluorfen, azafendin, cinidon-ethyl, oxadiargyl, oxadiazon, pentoxazone, flumipropyn, flupropacil, benzfendizone, nipyraclofen, fluazolate, thidiazimin or a compound having the structural formula

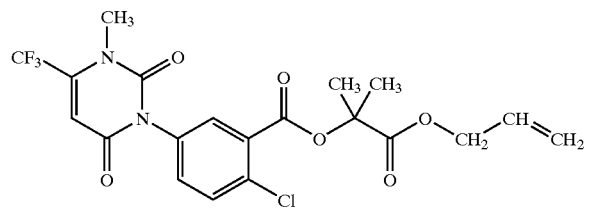

or combinations thereof.

The auxinic herbicidal agent may comprise one or more compounds selected from the group consisting of herbicidally active phenoxy, benzoic, pyridine, quinolinecarboxylic acid compounds, other than quinclorac, and amine, esters and inorganic salts thereof. The salts are preferably selected from a group consisting of, but are not limited to, methylamine, ethylamine, isopropylamine, monomethanolamine, monoethanolamine, monoisopropanolamine, dimethylamine, diethylamine, diisopropylamine, dimethanolamine, diethanolamine, diisopropanolamine, trimethylamine, triethyl amine, triisopropylamine, trimethanolamine, triethanolamine, triisopropanolamine, and ammonium, sodium, potassium, lithium, calcium salts of the above acids are also useful. The auxinic herbicidal acidic compounds may be selected from a group consisting of 2,4-dichlorophenoxyacetic acid(2,4-D), 2,4-dichlorophenoxypropionic acid(2,4-DP), 2,4-dichlorophenoxybutyric acid(2,4-DB), 2-methyl-4-chlorophenoxyacetic acid (MCPA), 2-methyl-4-chlorophenoxypropionic acid (MCPP), 2-methyl-4-chlorophenoxybutyric acid, 2,4,5-trichlorophenoxyacetic acid, 2,3,6-trichlorobenzoic acid, 3,6-dichloro-2-methoxybenzoic acid (dicamba), 2-methoxy-3,5,6-trichlorobenzoic acid, 4-chloro-2-oxobenzothiazolin-3-ylacetic acid, 4-amino-3,5,6-trichloropicolinic acid, trichloroacetic acid, 2,2-dichloropropionic acid, 3-amino-2,5-dichlorobenzoic acid, methane arsonic acid, 2,3,6-trichlorophenylacetic acid, 3,6-endoxohexahydrophthalic acid, 3,5,6-trichloro-4-aminopicolinic acid, 7-chloro-3-methyl-8-quinolinecarboxylic acid, ((4-amino-3,5-dichloro-6-fluoro-2-pyridinyl)oxy)acetic acid, 3,4,6-trichloro-2-pyridinyloxyacetic acid, 3,6-dichloro-2-pyridinecarboxylic acid, and 1-methylheptyl ester. Ester forms of the auxinic herbicidal agents include carbon chain lengths, either linear or branched, in which from $C_1$ to $C_{20}$ are present.

DETAILED DESCRIPTION OF THE INVENTION

The synergistic composition of this invention resulting from the combination of quinclorac, a herbicidal protox inhibitor and an auxinic herbicide as active agents normally would include any one of a number of well known inert ingredients, depending upon the nature of the product commercialized. Preferred synergistic formulations are as follows.

EXAMPLE 1

| Active Ingredient | Percent of Active Ingredient in Formulation |
|---|---|
| Quinclorac | 4.3% |
| Sulfentrazone | 0.3% |
| 2,4D | 8.6% |

EXAMPLE 2

| Active Ingredient | Percent of Active Ingredient in Formulation |
|---|---|
| Quinclorac | 4.3% |
| Carfentrazone-ethyl | 0.2% |
| MCPA | 12% |

EXAMPLE 3

| Active Ingredient | Percent of Active Ingredient in Formulation |
|---|---|
| Quinclorac | 4.3% |
| Sulfentrazone | 0.3% |
| MCPA | 12% |

The quinclorac content of the formulation is from about 1.0% to about 11.5%, more particularly from about 1.8% to about 4%, and preferably 4.3%. The carfentrazone-ethyl, sulfentrazone or pyraflufen-ethyl is from about 0.005% to about 0.06%, more particularly from about 0.01% to about 0.05%, and preferably from about 0.02% to about 0.03%. The auxinic herbicide is present in the formulation from about 1.7% to about 22.2%, more particularly from about 2.8% to about 16.3%, and preferably about 8.6%.

Greenhouse Tests

Pots of crabgrass, dandelion, white clover, and plantain grown in greenhouse soilless growth media were sprayed with a greenhouse pot sprayer at 43.46 gallons of spray solution/acre and allowed to stand in the greenhouse. Visual observation of the effects made by the herbicidal compositions on the plants in the test pots was recorded for control of crabgrass, dandelion, clover and plantain at 24 hours after treatment (HAT), 48 hours after treatment (HAT), 72 hours after treatment (HAT), 7 days after treatment (DAT), 14 days after treatment (DAT) and 21 days after treatment (DAT). A control rating scale of 1 to 9 was used to record the visual observation of the effect of the herbicidal composition on the plants over the time period of the tests. 1=no control, and 9=death of plant, with intervening numbers representing successive degrees of observed effectiveness of the herbicidal composition over time. The 1–9 control rating scale was converted to percent control in the test data charts that follow.

The test protocol of S. R. Colby as set out in his article entitled "Calculating Synergistic and Antagonistic Responses of Herbicide Compositions," received for publication Apr. 11, 1966, Contribution No. 3796 and Scientific Article No. 1271 of the Maryland Agricultural Experiment Station, Department pf Agronomy, University of Maryland was followed to evaluate the synergistic properties of the combination of quinclorac plus a herbicidal protox inhibitor, and a combination of quinclorac, plus a herbicidal protox inhibitor plus a herbicidal auxinic agent as compared with the individual herbicides, using Colby's formulas $E=X+Y-XY/100$ for a two herbicide combination, where E=the expected percent of inhibition of growth by herbicides, X=the percent inhibition of growth by herbicide A at p lb/A, and Y=the percent inhibition of growth by herbicide B at q lb/A, for a given combination of two herbicides. Colby's formula $E=X+Y+Z-(XY+XZ+YZ)/100+XYZ/10,000$, was used for the three-way herbicide combination evaluation, where E, X and Y are the same as in the two herbicide formula and Z=the percent inhibition of growth by the third herbicide.

It is recognized in the herbicide field that control of grassy weeds such as crabgrass can be obtained only over a time period of 10 to 14 days, whereas with the present synergistic combination, crabgrass control is obtained in as little as seven days as demonstrated by the test data set forth below.

| Test 1 Control (1–9) | | | | % Control | | | | | Crabgrass | | Dandelion | | Clover | |
|---|---|---|---|---|---|---|---|---|---|---|---|---|---|---|
| Crab-grass | Dan-delion | Clo-ver | Plan-tain | Crab-grass | Dan-delion | Clo-ver | Plan-tain | Treatment | Ex-pected | Actual | Ex-pected | Actual | Ex-pected | Actual |
| 24 HAT | | | | 24 HAT | | | | | | | | | | |
| 2 | 1 | 1 | | 22.2 | 11.1 | 11.1 | | Quinclorac @ 0.75 lbs/A | | | | | | |
| 2 | 1 | 1 | | 22.2 | 11.1 | 11.1 | | Quinclorac @ 0.375 lbs/A | | | | | | |
| 2 | 2 | 1 | | 22.2 | 22.2 | 11.1 | | Quinclorac @ 0.18 lbs/A | | | | | | |
| 3 | 3 | 3 | | 33.3 | 33.3 | 33.3 | | Carfentrazone @ 0.02 lbs/A | | | | | | |
| 2 | 4 | 3 | | 22.2 | 44.4 | 33.3 | | Carfentrazone @ 0.01 lbs/A | | | | | | |
| 2 | 3 | 1 | | 22.2 | 33.3 | 11.1 | | 2,4-D IOE @ 0.70 lbs/A | | | | | | |
| 4 | 4 | 4 | | 44.4 | 44.4 | 44.4 | | 0.75 Quinclorac + 0.02 Carfentrazone | 48.1 | 44.4 | 40.7 | 44.4 | 40.7 | 44.4 |
| 4 | 4 | 4 | | 44.4 | 44.4 | 44.4 | | 0.75 Quinclorac + 0.01 Carfentrazone | 39.5 | 44.4 | 50.6 | 44.4 | 40.7 | 44.4 |
| 3 | 4 | 3 | | 33.3 | 44.4 | 33.3 | | 0.375 Quinclorac + 0.02 Carfentrazone | 48.1 | 33.3 | 40.7 | 44.4 | 40.7 | 33.3 |
| 3 | 3 | 3 | | 33.3 | 33.3 | 33.3 | | 0.375 Quinclorac + 0.01 Carfentrazone | 39.5 | 33.3 | 50.6 | 33.3 | 40.7 | 33.3 |
| 3 | 5 | 4 | | 44.4 | 55.6 | 44.4 | | 0.18 Quinclorac + 0.02 Carfentrazone | 48.1 | 33.3 | 48.1 | 55.6 | 40.7 | 44.4 |
| 4 | 4 | 4 | | 44.4 | 44.4 | 44.4 | | 0.18 Quinclorac + 0.01 Carfentrazone | 39.5 | 44.4 | 56.8 | 44.4 | 40.7 | 44.4 |
| 5 | 5 | 4 | | 44.4 | 55.6 | 44.4 | | 0.75 Quinclorac + 0.02 Carfentrazone + 0.70 2,4-D IOE | 59.7 | 55.6 | 60.5 | 55.6 | 47.3 | 44.4 |
| 5 | — | 4 | | 55.6 | 55.6 | 44.4 | | 0.75 Quinclorac + 0.01 Carfentrazone + 0.70 2,4-D IOE | 52.9 | 55.6 | 67.1 | 55.6 | 47.3 | 44.4 |
| 5 | 5 | 4 | | 44.4 | 55.6 | 44.4 | | 0.375 Quinclorac + 0.02 Carfentrazone + 0.70 2,4-D IOE | 59.7 | 55.6 | 60.5 | 55.6 | 47.3 | 44.4 |
| 4 | 4 | 4 | | 44.4 | 44.4 | 44.4 | | 0.375 Quinclorac + 0.01 Carfentrazone + 0.70 2,4-D IOE | 52.9 | 44.4 | 67.1 | 44.4 | 47.3 | 44.4 |
| 48 HAT | | | | 48 HAT | | | | | | | | | | |
| 4 | 3 | 3 | | 44.4 | 33.3 | 33.3 | | Quinclorac @ 0.75 lbs/A | | | | | | |
| 4 | 3 | 3 | | 44.4 | 33.3 | 33.3 | | Quinclorac @ 0.375 lbs/A | | | | | | |
| 3 | 3 | 2 | | 33.3 | 33.3 | 22.2 | | Quinclorac @ 0.18 lbs/A | | | | | | |
| 5 | 5 | 5 | | 55.6 | 55.6 | 55.6 | | Carfentrazone @ 0.02 lbs/A | | | | | | |
| 3 | 5 | 5 | | 33.3 | 55.6 | 55.6 | | Carfentrazone @ 0.01 lbs/A | | | | | | |
| 4 | 4 | 4 | | 44.4 | 44.4 | 44.4 | | 2,4-D IOE @ 0.70 lbs/A | | | | | | |
| 5 | 6 | 6 | | 55.6 | 66.7 | 66.7 | | 0.75 Quinclorac + 0.02 Carfentrazone | 75.3 | 55.6 | 70.4 | 66.7 | 70.4 | 66.7 |
| 6 | 7 | 7 | | 66.7 | 77.8 | 77.8 | | 0.75 Quinclorac + 0.01 Carfentrazone | 63.0 | 66.7 | 70.4 | 77.8 | 70.4 | 77.8 |
| 5 | 7 | 7 | | 55.6 | 77.8 | 77.8 | | 0.375 Quinclorac + 0.02 Carfentrazone | 75.3 | 55.6 | 70.4 | 77.8 | 70.4 | 77.8 |
| 7 | 7 | 7 | | 77.8 | 77.8 | 77.8 | | 0.375 Quinclorac + 0.01 Carfentrazone | 63.0 | 77.8 | 70.4 | 77.8 | 70.4 | 77.8 |
| 7 | 8 | 7 | | 77.8 | 88.9 | 77.8 | | 0.18 Quinclorac + 0.02 Carfentrazone | 70.4 | 77.8 | 70.4 | 88.9 | 65.4 | 77.8 |
| 7 | 7 | 7 | | 77.8 | 77.8 | 77.8 | | 0.18 Quinclorac + 0.01 Carfentrazone | 55.6 | 77.8 | 70.4 | 77.8 | 65.4 | 77.8 |
| 8 | 8 | 7 | | 88.9 | 88.9 | 77.8 | | 0.75 Quinclorac + 0.02 Carfentrazone + 0.70 2,4-D IOE | 86.3 | 88.9 | 83.5 | 88.9 | 83.5 | 77.8 |
| 8 | 8 | 8 | | 88.9 | 88.9 | 88.9 | | 0.75 Quinclorac + 0.01 Carfentrazone + 0.70 2,4-D IOE | 79.4 | 88.9 | 83.5 | 88.9 | 83.5 | 88.9 |

-continued

| Test 1 Control (1–9) | | | | % Control | | | | | Crabgrass | | Dandelion | | Clover | |
|---|---|---|---|---|---|---|---|---|---|---|---|---|---|---|
| Crab-grass | Dan-delion | Clo-ver | Plan-tain | Crab-grass | Dan-delion | Clo-ver | Plan-tain | Treatment | Ex-pected | Actual | Ex-pected | Actual | Ex-pected | Actual |
| 7 | 7 | 7 | | 77.8 | 77.8 | 77.8 | | 0.375 Quinclorac + 0.02 Carfentrazone + 0.70 2,4-D IOE | 86.3 | 77.8 | 83.5 | 77.8 | 83.5 | 77.8 |
| 7 | 6 | 7 | | 77.8 | 66.7 | 77.8 | | 0.375 Quinclorac + 0.01 Carfentrazone + 0.70 2,4-D IOE | 79.4 | 77.8 | 83.5 | 66.7 | 83.5 | 77.8 |
| | | 7 DAT | | | | 7 DAT | | | | | | | | |
| 4 | 3 | 3 | | 44.4 | 33.3 | 33.3 | | Quinclorac @ 0.75 lbs/A | | | | | | |
| 4 | 3 | 3 | | 44.4 | 33.3 | 33.3 | | Quinclorac @ 0.375 lbs/A | | | | | | |
| 4 | 3 | 3 | | 44.4 | 33.3 | 33.3 | | Quinclorac @ 0.18 lbs/A | | | | | | |
| 7 | 8 | 6 | | 77.8 | 88.9 | 66.7 | | Carfentrazone @ 0.02 lbs/A | | | | | | |
| 7 | 8 | 6 | | 77.8 | 88.9 | 66.7 | | Carfentrazone @ 0.01 lbs/A | | | | | | |
| 4 | 6 | 4 | | 44.4 | 66.7 | 44.4 | | 2,4-D IOE @ 0.70 lbs/A | | | | | | |
| 8 | 8 | 8 | | 88.9 | 88.9 | 88.9 | | 0.75 Quinclorac + 0.02 Carfentrazone | 87.7 | 88.9 | 92.6 | 88.9 | 77.8 | 88.9 |
| 8 | 8 | 8 | | 88.9 | 88.9 | 88.9 | | 0.75 Quinclorac + 0.01 Carfentrazone | 87.7 | 88.9 | 92.6 | 88.9 | 77.8 | 88.9 |
| 8 | 8 | 8 | | 88.9 | 88.9 | 88.9 | | 0.375 Quinclorac + 0.02 Carfentrazone | 87.7 | 88.9 | 92.6 | 88.9 | 77.8 | 88.9 |
| 8 | 8 | 8 | | 88.9 | 88.9 | 88.9 | | 0.375 Quinclorac + 0.01 Carfentrazone | 87.7 | 88.9 | 92.6 | 88.9 | 77.8 | 88.9 |
| 8 | 9 | 8 | | 88.9 | 100.0 | 88.9 | | 0.18 Quinclorac + 0.02 Carfentrazone | 87.7 | 88.9 | 92.6 | 100.0 | 77.8 | 88.9 |
| 8 | 9 | 8 | | 88.9 | 100.0 | 88.9 | | 0.18 Quinclorac + 0.01 Carfentrazone | 87.7 | 88.9 | 92.6 | 100.0 | 77.8 | 88.9 |
| 8 | 9 | 8 | | 88.9 | 100.0 | 88.9 | | 0.75 Quinclorac + 0.02 Carfentrazone + 0.70 2,4-D IOE | 93.1 | 88.9 | 97.5 | 100.0 | 87.7 | 88.9 |
| 8 | 9 | 8 | | 88.9 | 100.0 | 88.9 | | 0.75 Quinclorac + 0.01 Carfentrazone + 0.70 2,4-D IOE | 93.1 | 88.9 | 97.5 | 100.0 | 87.7 | 88.9 |
| 8 | 9 | 8 | | 88.9 | 100.0 | 88.9 | | 0.375 Quinclorac + 0.02 Carfentrazone + 0.70 2,4-D IOE | 93.1 | 88.9 | 97.5 | 100.0 | 87.7 | 88.9 |
| 8 | 9 | 8 | | 88.9 | 100.0 | 88.9 | | 0.375 Quinclorac + 0.01 Carfentrazone + 0.70 2,4-D IOE | 93.1 | 88.9 | 97.5 | 100.0 | 87.7 | 88.9 |
| | | 14 DAT | | | | 14 DAT | | | | | | | | |
| 5 | 6 | 8 | | 55.6 | 66.7 | 88.9 | | Quinclorac @ 0.75 lbs/A | | | | | | |
| 5 | 7 | 9 | | 55.6 | 77.8 | 100.0 | | Quinclorac @ 0.375 lbs/A | | | | | | |
| 7 | 8 | 9 | | 77.8 | 88.9 | 100.0 | | Quinclorac @ 0.18 lbs/A | | | | | | |
| 3 | 9 | 9 | | 33.3 | 100.0 | 100.0 | | Carfentrazone @ 0.02 lbs/A | | | | | | |
| 3 | 8 | 7 | | 33.3 | 88.9 | 77.8 | | Carfentrazone @ 0.01 lbs/A | | | | | | |
| 3 | 9 | 8 | | 33.3 | 100.0 | 88.9 | | 2,4-D IOE @ 0.70 lbs/A | | | | | | |
| 8 | 9 | 9 | | 88.9 | 100.0 | 100.0 | | 0.75 Quinclorac + 0.02 Carfentrazone | 70.4 | 88.4 | 100.0 | 100.0 | 100.0 | 100.0 |
| 8 | 9 | 9 | | 88.9 | 100.0 | 100.0 | | 0.75 Quinclorac + 0.01 Carfentrazone | 70.4 | 88.9 | 96.3 | 100.0 | 97.5 | 100.0 |
| 7 | 9 | 9 | | 77.8 | 100.0 | 100.0 | | 0.375 Quinclorac + 0.02 Carfentrazone | 70.4 | 77.8 | 100.0 | 100.0 | 100.0 | 100.0 |
| 6 | 9 | 9 | | 66.7 | 100.0 | 100.0 | | 0.375 Quinclorac + 0.01 Carfentrazone | 70.4 | 66.7 | 97.5 | 100.0 | 100.0 | 100.0 |
| 6 | 9 | 8 | | 66.7 | 100.0 | 88.9 | | 0.18 Quinclorac + 0.02 Carfentrazone | 85.2 | 66.7 | 100.0 | 100.0 | 100.0 | 88.9 |
| 7 | 9 | 8 | | 77.8 | 100.0 | 88.9 | | 0.18 Quinclorac + 0.01 Carfentrazone | 85.2 | 77.8 | 98.8 | 100.0 | 100.0 | 88.9 |
| 7 | 9 | 9 | | 77.8 | 100.0 | 100.0 | | 0.75 Quinclorac + 0.02 Carfentrazone + 0.70 2,4-D IOE | 80.2 | 77.8 | 100.0 | 100.0 | 100.0 | 100.0 |
| 8 | 9 | 9 | | 88.9 | 100.0 | 100.0 | | 0.75 Quinclorac + 0.01 Carfentrazone + 0.70 2,4-D IOE | 80.2 | 88.9 | 100.0 | 100.0 | 99.7 | 100.0 |
| 8 | 9 | 9 | | 88.4 | 100.0 | 100.0 | | 0.375 Quinclorac + 0.02 Carfentrazone + 0.70 2,4-D IOE | 80.2 | 88.4 | 100.0 | 100.0 | 100.0 | 100.0 |
| 8 | 9 | 9 | | 88.9 | 100.0 | 100.0 | | 0.375 Quinclorac + 0.01 Carfentrazone + 0.70 2,4-D IOE | 80.2 | 88.9 | 100.0 | 100.0 | 100.0 | 100.0 |

| Test 2 Control (1–9) | | | | % Control | | | | | Crabgrass | | Dandelion | | Clover | |
|---|---|---|---|---|---|---|---|---|---|---|---|---|---|---|
| Crab-grass | Dan-delion | Clo-ver | Plan-tain | Crab-grass | Dan-delion | Clo-ver | Plan-tain | Treatment | Ex-pected | Actual | Ex-pected | Actual | Ex-pected | Actual |
| 24 HAT | | | | 24 HAT | | | | | | | | | | |
| 2 | 2 | 2 | | 22.2 | 22.2 | 22.2 | | Quinclorac @ 0.75 lbs/A | | | | | | |
| 2 | 2 | 2 | | 22.2 | 22.2 | 22.2 | | Quinclorac @ 0.375 lbs/A | | | | | | |
| 3 | 2 | 2 | | 33.3 | 22.2 | 22.2 | | Quinclorac @ 0.18 lbs/A | | | | | | |
| 4 | 2 | 2 | | 44.4 | 22.2 | 22.2 | | Sulfentrazone @ 0.03 lbs/A | | | | | | |
| 3 | 2 | 2 | | 33.3 | 22.2 | 22.2 | | Sulfentrazone @ 0.02 lbs/A | | | | | | |
| 3 | 3 | 3 | | 33.3 | 33.3 | 33.3 | | 2,4-D IOE @ 0.70 lbs/A | | | | | | |
| 4 | 3 | 3 | | 44.4 | 33.3 | 33.3 | | 0.75 Quinclorac + 0.03 Sulfentrazone | 56.8 | 44.4 | 39.5 | 33.3 | 39.5 | 33.3 |
| 5 | 3 | 5 | | 55.6 | 33.3 | 55.6 | | 0.75 Quinclorac + 0.02 Sulfentrazone | 48.1 | 55.6 | 39.5 | 33.3 | 39.5 | 55.6 |
| 5 | 3 | 5 | | 55.6 | 33.3 | 55.6 | | 0.375 Quinclorac + 0.03 Sulfentrazone | 56.8 | 55.6 | 39.5 | 33.3 | 39.5 | 55.6 |
| 5 | 3 | 5 | | 55.6 | 33.3 | 55.6 | | 0.375 Quinclorac + 0.02 Sulfentrazone | 48.1 | 55.6 | 39.5 | 33.3 | 39.5 | 55.6 |
| 4 | 4 | 4 | | 44.4 | 44.4 | 44.4 | | 0.18 Quinclorac + 0.03 Sulfentrazone | 63.0 | 44.4 | 39.5 | 44.4 | 39.5 | 44.4 |
| 5 | 4 | 3 | | 55.6 | 44.4 | 33.3 | | 0.18 Quinclorac + 0.02 Sulfentrazone | 55.6 | 55.6 | 39.5 | 44.4 | 39.5 | 33.3 |
| 6 | 5 | 6 | | 66.7 | 55.6 | 66.7 | | 0.75 Quinclorac + 0.03 Sulfentrazone + 0.70 2,4-D IOE | 71.2 | 66.7 | 59.7 | 55.6 | 59.7 | 66.7 |
| 6 | 5 | 6 | | 66.7 | 55.6 | 66.7 | | 0.75 Quinclorac + 0.02 Sulfentrazone + 0.70 2,4-D IOE | 65.4 | 66.7 | 59.7 | 55.6 | 59.7 | 66.7 |
| 6 | 5 | 6 | | 66.7 | 55.6 | 66.7 | | 0.375 Quinclorac + 0.03 Sulfentrazone + 0.70 2,4-D IOE | 71.2 | 66.7 | 59.7 | 55.6 | 59.7 | 66.7 |
| 6 | 5 | 6 | | 66.7 | 55.6 | 66.7 | | 0.375 Quinclorac + 0.02 Sulfentrazone + 0.70 2,4-D IOE | 65.4 | 66.7 | 59.7 | 55.6 | 59.7 | 66.7 |
| 72 HAT | | | | 72 HAT | | | | | | | | | | |
| 4 | 3 | 3 | | 44.4 | 33.3 | 33.3 | | Quinclorac @ 0.75 lbs/A | | | | | | |
| 3 | 3 | 3 | | 33.3 | 33.3 | 33.3 | | Quinclorac @ 0.375 lbs/A | | | | | | |
| 4 | 5 | 3 | | 44.4 | 55.6 | 33.3 | | Quinclorac @ 0.18 lbs/A | | | | | | |
| 3 | 4 | 2 | | 33.3 | 44.4 | 22.2 | | Sulfentrazone @ 0.03 lbs/A | | | | | | |
| 3 | 4 | 3 | | 33.3 | 44.4 | 33.3 | | Sulfentrazone @ 0.02 lbs/A | | | | | | |
| 6 | 6 | 6 | | 66.7 | 66.7 | 66.7 | | 2,4-D IOE @ 0.70 lbs/A | | | | | | |
| 7 | 8 | 7 | | 77.8 | 88.9 | 77.8 | | 0.75 Quinclorac + 0.03 Sulfentrazone | 63.0 | 77.8 | 63.0 | 88.9 | 48.1 | 77.8 |
| 7 | 8 | 6 | | 77.8 | 88.9 | 66.7 | | 0.75 Quinclorac + 0.02 Sulfentrazone | 63.0 | 77.8 | 63.0 | 88.9 | 55.6 | 66.7 |
| 5 | 8 | 4 | | 55.6 | 88.9 | 44.4 | | 0.375 Quinclorac + 0.03 Sulfentrazone | 55.6 | 55.6 | 63.0 | 88.9 | 48.1 | 44.4 |
| 6 | 8 | 5 | | 66.7 | 88.9 | 55.6 | | 0.375 Quinclorac + 0.02 Sulfentrazone | 55.6 | 66.7 | 63.0 | 88.9 | 55.6 | 55.6 |
| 6 | 8 | 4 | | 66.7 | 88.9 | 44.4 | | 0.18 Quinclorac + 0.03 Sulfentrazone | 63.0 | 66.7 | 75.3 | 88.9 | 48.1 | 44.4 |
| 6 | 8 | 4 | | 66.7 | 88.9 | 44.4 | | 0.18 Quinclorac + 0.02 Sulfentrazone | 63.0 | 66.7 | 75.3 | 88.9 | 55.6 | 44.4 |
| 8 | 8 | 8 | | 88.9 | 88.9 | 88.9 | | 0.75 Quinclorac + 0.03 Sulfentrazone + 0.70 2,4-D IOE | 87.7 | 88.9 | 87.7 | 88.9 | 82.7 | 88.9 |
| 8 | 8 | 8 | | 88.9 | 88.9 | 88.9 | | 0.75 Quinclorac + 0.02 Sulfentrazone + 0.70 2,4-D IOE | 87.7 | 88.9 | 87.7 | 88.9 | 85.2 | 88.9 |
| 8 | 8 | 8 | | 88.9 | 88.9 | 88.9 | | 0.375 Quinclorac + 0.03 Sulfentrazone + 0.70 2,4-D IOE | 85.2 | 88.9 | 87.7 | 88.9 | 82.7 | 88.9 |
| 8 | 8 | 8 | | 88.9 | 88.9 | 88.9 | | 0.375 Quinclorac + 0.02 Sulfentrazone + 0.70 2,4-D IOE | 85.2 | 88.9 | 87.7 | 88.9 | 85.2 | 88.9 |
| 7 DAT | | | | 7 DAT | | | | | | | | | | |
| 7 | 3 | 7 | | 77.8 | 33.3 | 77.8 | | Quinclorac @ 0.75 lbs/A | | | | | | |
| 7 | 3 | 7 | | 77.8 | 33.3 | 77.8 | | Quinclorac @ 0.375 lbs/A | | | | | | |
| 3 | 8 | 6 | | 33.3 | 88.9 | 66.7 | | Quinclorac @ 0.18 lbs/A | | | | | | |
| 2 | 8 | 5 | | 22.2 | 88.9 | 55.6 | | Sulfentrazone @ 0.03 lbs/A | | | | | | |
| 2 | 8 | 7 | | 22.2 | 88.9 | 77.8 | | Sulfentrazone @ 0.02 lbs/A | | | | | | |
| 2 | 8 | 6 | | 22.2 | 88.9 | 66.7 | | 2,4-D IOE @ 0.70 lbs/A | | | | | | |
| 8 | 8 | 8 | | 88.9 | 88.9 | 88.9 | | 0.75 Quinclorac + 0.03 Sulfentrazone | 82.7 | 88.9 | 92.6 | 88.9 | 90.1 | 88.9 |

-continued

| Test 2 Control (1–9) | | | | % Control | | | | | Crabgrass | | Dandelion | | Clover | |
|---|---|---|---|---|---|---|---|---|---|---|---|---|---|---|
| Crab-grass | Dan-delion | Clo-ver | Plan-tain | Crab-grass | Dan-delion | Clo-ver | Plan-tain | Treatment | Ex-pected | Actual | Ex-pected | Actual | Ex-pected | Actual |
| 7 | 8 | 6 | | 77.8 | 88.9 | 66.7 | | 0.75 Quinclorac + 0.02 Sulfentrazone | 82.7 | 77.8 | 92.6 | 88.9 | 95.1 | 66.7 |
| 8 | 8 | 8 | | 88.9 | 88.9 | 88.9 | | 0.375 Quinclorac + 0.03 Sulfentrazone | 82.7 | 88.9 | 92.6 | 88.9 | 90.1 | 88.9 |
| 6 | 8 | 7 | | 66.7 | 88.9 | 77.8 | | 0.375 Quinclorac + 0.02 Sulfentrazone | 82.7 | 66.7 | 92.6 | 88.9 | 95.1 | 77.8 |
| 6 | 8 | 7 | | 66.7 | 88.9 | 77.8 | | 0.18 Quinclorac + 0.03 Sulfentrazone | 48.1 | 66.7 | 98.8 | 88.9 | 85.2 | 77.8 |
| 6 | 8 | 7 | | 66.7 | 88.9 | 77.8 | | 0.18 Quinclorac + 0.02 Sulfentrazone | 48.1 | 66.7 | 98.8 | 88.9 | 92.6 | 77.8 |
| 8 | 9 | 8 | | 88.9 | 100.0 | 88.9 | | 0.75 Quinclorac + 0.03 Sulfentrazone + 0.70 2,4-D IOE | 86.6 | 88.9 | 99.2 | 100.0 | 96.7 | 88.9 |
| 8 | 9 | 8 | | 88.9 | 100.0 | 88.9 | | 0.75 Quinclorac + 0.02 Sulfentrazone + 0.70 2,4-D IOE | 86.6 | 88.9 | 99.2 | 100.0 | 98.4 | 88.9 |
| 8 | 9 | 8 | | 88.9 | 100.0 | 88.9 | | 0.375 Quinclorac + 0.03 Sulfentrazone + 0.70 2,4-D IOE | 86.6 | 88.9 | 99.2 | 100.0 | 96.7 | 88.9 |
| 8 | 9 | 8 | | 88.9 | 100.0 | 88.9 | | 0.375 Quinclorac + 0.02 Sulfentrazone + 0.70 2,4-D IOE | 86.6 | 88.9 | 99.2 | 100.0 | 98.4 | 88.9 |
| | 14 DAT | | | | 14 DAT | | | | | | | | | |
| 8 | 6 | 9 | | 88.9 | 66.7 | 100.0 | | Quinclorac @ 0.75 lbs/A | | | | | | |
| 7 | 8 | 9 | | 77.8 | 88.9 | 100.0 | | Quinclorac @ 0.375 lbs/A | | | | | | |
| 5 | 8 | 9 | | 55.6 | 88.9 | 100.0 | | Quinclorac @ 0.18 lbs/A | | | | | | |
| 2 | 8 | 6 | | 22.2 | 88.9 | 66.7 | | Sulfentrazone @ 0.03 lbs/A | | | | | | |
| 2 | 8 | 7 | | 22.2 | 88.9 | 77.8 | | Sulfentrazone @ 0.02 lbs/A | | | | | | |
| 2 | 9 | 9 | | 22.2 | 100.0 | 100.0 | | 2,4-D IOE @ 0.70 lbs/A | | | | | | |
| 8 | 9 | 9 | | 88.9 | 100.0 | 100.0 | | 0.75 Quinclorac + 0.03 Sulfentrazone | 91.4 | 88.9 | 96.3 | 100.0 | 100.0 | 100.0 |
| 7 | 9 | 9 | | 77.8 | 100.0 | 100.0 | | 0.75 Quinclorac + 0.02 Sulfentrazone | 91.4 | 77.8 | 96.3 | 100.0 | 100.0 | 100.0 |
| 7 | 9 | 9 | | 77.8 | 100.0 | 100.0 | | 0.375 Quinclorac + 0.03 Sulfentrazone | 82.7 | 77.8 | 98.8 | 100.0 | 100.0 | 100.0 |
| 6 | 9 | 9 | | 66.7 | 100.0 | 100.0 | | 0.375 Quinclorac + 0.02 Sulfentrazone | 82.7 | 66.7 | 98.8 | 100.0 | 100.0 | 100.0 |
| 6 | 9 | 9 | | 66.7 | 100.0 | 100.0 | | 0.18 Quinclorac + 0.03 Sulfentrazone | 65.4 | 66.7 | 98.8 | 100.0 | 100.0 | 100.0 |
| 7 | 9 | 9 | | 77.8 | 100.0 | 100.0 | | 0.18 Quinclorac + 0.02 Sulfentrazone | 65.4 | 77.8 | 98.8 | 100.0 | 100.0 | 100.0 |
| 8 | 9 | 9 | | 88.9 | 100.0 | 100.0 | | 0.75 Quinclorac + 0.03 Sulfentrazone + 0.70 2,4-D IOE | 93.3 | 88.9 | 100.0 | 100.0 | 100.0 | 100.0 |
| 8 | 9 | 9 | | 88.9 | 100.0 | 100.0 | | 0.75 Quinclorac + 0.02 Sulfentrazone + 0.70 2,4-D IOE | 93.3 | 88.9 | 100.0 | 100.0 | 100.0 | 100.0 |
| 8 | 9 | 9 | | 88.9 | 100.0 | 100.0 | | 0.375 Quinclorac + 0.03 Sulfentrazone + 0.70 2,4-D IOE | 86.6 | 88.9 | 100.0 | 100.0 | 100.0 | 100.0 |
| 7 | 9 | 9 | | 77.8 | 100.0 | 100.0 | | 0.375 Quinclorac + 0.02 Sulfentrazone + 0.70 2,4-D IOE | 86.6 | 77.8 | 100.0 | 100.0 | 100.0 | 100.0 |

| Test 3 Control (1–9) | | | | % Control | | | | | Crabgrass | | Dandelion | | Clover | | Plantain | |
|---|---|---|---|---|---|---|---|---|---|---|---|---|---|---|---|---|
| Crab-grass | Dan-delion | Clo-ver | Plan-tain | Crab-grass | Dan-delion | Clo-ver | Plan-tain | Treatment | Ex-pected | Actual | Ex-pected | Actual | Ex-pected | Actual | Ex-pected | Actual |
| | 24 HAT | | | | 24 HAT | | | | | | | | | | | |
| 1 | 1 | 1 | 1 | 11.1 | 11.1 | 11.1 | 11.1 | Quinclorac @ 0.75 lbs/A | | | | | | | | |
| 1 | 1 | 1 | 1 | 11.1 | 11.1 | 11.1 | 11.1 | Quinclorac @ 0.375 lbs/A | | | | | | | | |

-continued

| Test 3 Control (1–9) | | | | % Control | | | | Treatment | Crabgrass | | Dandelion | | Clover | | Plantain | |
|---|---|---|---|---|---|---|---|---|---|---|---|---|---|---|---|---|
| Crab-grass | Dan-de-lion | Clo-ver | Plan-tain | Crab-grass | Dan-de-lion | Clo-ver | Plan-tain | | Ex-pected | Actual | Ex-pected | Actual | Ex-pected | Actual | Ex-pected | Actual |
| 1 | 1 | 1 | 1 | 11.1 | 11.1 | 11.1 | 11.1 | Quinclorac @ 0.18 lbs/A | | | | | | | | |
| 1 | 3 | 2 | 4 | 11.1 | 33.3 | 22.2 | 44.4 | Sulfen-trazone @ 0.03 lbs/A | | | | | | | | |
| 1 | 3 | 3 | 4 | 11.1 | 33.3 | 33.3 | 44.4 | Sulfen-trazone @ 0.02 lbs/A | | | | | | | | |
| 1 | 3 | 4 | 4 | 11.1 | 33.3 | 44.4 | 44.4 | MCPA IOE @ 1.10 lbs/A | | | | | | | | |
| 1 | 2 | 2 | 4 | 11.1 | 22.2 | 22.2 | 44.4 | 0.75 Quinclorac + 0.03 Sulfentrazone | 21.0 | 11.1 | 40.7 | 22.2 | 30.9 | 22.2 | 50.6 | 44.4 |
| 1 | 2 | 2 | 4 | 11.1 | 22.2 | 22.2 | 44.4 | 0.75 Quinclorac + 0.02 Sulfentrazone | 21.0 | 11.1 | 40.7 | 22.2 | 40.7 | 22.2 | 50.6 | 44.4 |
| 1 | 2 | 2 | 4 | 11.1 | 22.2 | 22.2 | 44.4 | 0.375 Quinclorac + 0.03 Sulfentrazone | 21.0 | 11.1 | 40.7 | 22.2 | 30.9 | 22.2 | 50.6 | 44.4 |
| 1 | 3 | 2 | 5 | 11.1 | 33.3 | 22.2 | 55.6 | 0.375 Quinclorac + 0.02 Sulfentrazone | 21.0 | 11.1 | 40.7 | 33.3 | 40.7 | 22.2 | 50.6 | 55.6 |
| 1 | 3 | 3 | 5 | 11.1 | 33.3 | 33.3 | 55.6 | 0.18 Quinclorac + 0.03 Sulfentrazone | 21.0 | 11.1 | 40.7 | 33.3 | 30.9 | 33.3 | 50.6 | 55.6 |
| 1 | 3 | 3 | 5 | 11.1 | 33.3 | 33.3 | 55.6 | 0.18 Quinclorac + 0.02 Sulfentrazone | 21.0 | 11.1 | 40.7 | 33.3 | 40.7 | 33.3 | 50.6 | 55.6 |
| 1 | 3 | 4 | 5 | 11.1 | 33.3 | 44.4 | 55.6 | 0.75 Quinclorac + 0.03 Sulfen-trazone + 1.10 MCPA IOE | 29.8 | 11.1 | 60.5 | 33.3 | 61.6 | 44.4 | 72.6 | 55.6 |
| 1 | 3 | 3 | 4 | 11.1 | 33.3 | 33.3 | 44.4 | 0.75 Quinclorac + 0.02 Sulfen-trazone + 1.10 MCPA IOE | 29.8 | 11.1 | 60.5 | 33.3 | 67.1 | 33.3 | 72.6 | 44.4 |
| 1 | 3 | 4 | 4 | 11.1 | 33.3 | 44.4 | 44.4 | 0.375 Quinclorac + 0.03 Sulfen-trazone + 1.10 MCPA IOE | 29.8 | 11.1 | 60.5 | 33.3 | 61.6 | 44.4 | 72.6 | 44.4 |
| 1 | 3 | 4 | 4 | 11.1 | 33.3 | 44.4 | 44.4 | 0.375 Quinclorac + 0.02 Sulfen-trazone + 1.10 MCPA IOE | 29.8 | 11.1 | 60.5 | 33.3 | 67.1 | 44.4 | 72.6 | 44.4 |
| 72 HAT | | | | 72 HAT | | | | | | | | | | | | |
| 2 | 2 | 2 | 2 | 22.2 | 22.2 | 22.2 | 22.2 | Quinclorac @ 0.75 lbs/A | | | | | | | | |
| 1 | 2 | 2 | 2 | 11.1 | 22.2 | 22.2 | 22.2 | Quinclorac @ 0.375 lbs/A | | | | | | | | |
| 1 | 2 | 2 | 2 | 11.1 | 22.2 | 22.2 | 22.2 | Quinclorac @ 0.18 lbs/A | | | | | | | | |
| 4 | 5 | 3 | 6 | 44.4 | 55.6 | 33.3 | 66.7 | Sulfen-trazone @ 0.03 lbs/A | | | | | | | | |
| 2 | 3 | 2 | 8 | 22.2 | 33.3 | 22.2 | 88.9 | Sulfen-trazone @ 0.02 lbs/A | | | | | | | | |

-continued

| Test 3 Control (1–9) | | | | % Control | | | | | Crabgrass | | Dandelion | | Clover | | Plantain | |
|---|---|---|---|---|---|---|---|---|---|---|---|---|---|---|---|---|
| Crab-grass | Dan-de-lion | Clo-ver | Plan-tain | Crab-grass | Dan-de-lion | Clo-ver | Plan-tain | Treatment | Ex-pected | Actual | Ex-pected | Actual | Ex-pected | Actual | Ex-pected | Actual |
| 1 | 5 | 4 | 4 | 11.1 | 55.6 | 44.4 | 44.4 | MCPA IOE @ 1.10 lbs/A | | | | | | | | |
| 3 | 5 | 4 | 8 | 33.3 | 55.6 | 44.4 | 88.9 | 0.75 Quinclorac + 0.03 Sulfentrazone | 56.8 | 33.3 | 65.4 | 55.6 | 48.1 | 44.4 | 74.1 | 88.9 |
| 3 | 5 | 5 | 7 | 33.3 | 55.6 | 55.6 | 77.8 | 0.75 Quinclorac + 0.02 Sulfentrazone | 39.5 | 33.3 | 48.1 | 55.6 | 39.5 | 55.6 | 91.4 | 77.8 |
| 5 | 5 | 4 | 8 | 55.6 | 55.6 | 44.4 | 88.9 | 0.375 Quinclorac + 0.03 Sulfentrazone | 50.6 | 55.6 | 65.4 | 55.6 | 48.1 | 44.4 | 74.1 | 88.9 |
| 4 | 5 | 3 | 7 | 44.4 | 55.6 | 33.3 | 77.8 | 0.375 Quinclorac + 0.02 Sulfentrazone | 30.9 | 44.4 | 48.1 | 55.6 | 39.5 | 33.3 | 91.4 | 77.8 |
| 5 | 5 | 4 | 8 | 55.6 | 55.6 | 44.4 | 88.9 | 0.18 Quinclorac + 0.03 Sulfentrazone | 50.6 | 55.6 | 65.4 | 55.6 | 48.1 | 44.4 | 74.1 | 88.9 |
| 4 | 4 | 5 | 7 | 44.4 | 44.4 | 55.6 | 77.8 | 0.18 Quinclorac + 0.02 Sulfentrazone | 30.9 | 44.4 | 48.1 | 44.4 | 39.5 | 55.6 | 91.4 | 77.8 |
| 7 | 6 | 6 | 8 | 77.8 | 66.7 | 66.7 | 88.9 | 0.75 Quinclorac + 0.03 Sulfentrazone + 1.10 MCPA IOE | 61.6 | 77.8 | 84.6 | 66.7 | 71.2 | 66.7 | 85.6 | 88.9 |
| 7 | 6 | 6 | 8 | 77.8 | 66.7 | 66.7 | 88.9 | 0.75 Quinclorac + 0.02 Sulfentrazone + 1.10 MCPA IOE | 46.2 | 77.8 | 77.0 | 66.7 | 66.4 | 66.7 | 95.2 | 88.9 |
| 7 | 6 | 6 | 8 | 77.8 | 66.7 | 66.7 | 88.9 | 0.375 Quinclorac + 0.03 Sulfentrazone + 1.10 MCPA IOE | 56.1 | 77.8 | 84.6 | 66.7 | 71.2 | 66.7 | 85.6 | 88.9 |
| 7 | 6 | 6 | 8 | 77.8 | 66.7 | 66.7 | 88.9 | 0.375 Quinclorac + 0.02 Sulfentrazone + 1.10 MCPA IOE | 38.5 | 77.8 | 77.0 | 66.7 | 66.4 | 66.7 | 95.2 | 88.9 |
| 7 DAT | | | | 7 DAT | | | | | | | | | | | | |
| 2 | 2 | 4 | 3 | 22.2 | 22.2 | 44.4 | 33.3 | Quinclorac @ 0.75 lbs/A | | | | | | | | |
| 2 | 2 | 4 | 3 | 22.2 | 22.2 | 44.4 | 33.3 | Quinclorac @ 0.375 lbs/A | | | | | | | | |
| 2 | 2 | 4 | 2 | 22.2 | 22.2 | 44.4 | 22.2 | Quinclorac @ 0.18 lbs/A | | | | | | | | |
| 5 | 6 | 4 | 8 | 55.6 | 66.7 | 44.4 | 88.9 | Sulfentrazone @ 0.03 lbs/A | | | | | | | | |
| 4 | 4 | 3 | 9 | 44.4 | 44.4 | 33.3 | 100.0 | Sulfentrazone @ 0.02 lbs/A | | | | | | | | |
| 1 | 6 | 6 | 6 | 11.1 | 66.7 | 66.7 | 66.7 | MCPA IOE @ 1.10 lbs/A | | | | | | | | |
| 6 | 6 | 4 | 9 | 66.7 | 66.7 | 44.4 | 100.0 | 0.75 Quinclorac + 0.03 Sulfentrazone | 65.4 | 66.7 | 74.1 | 66.7 | 69.1 | 44.4 | 92.6 | 100.0 |

-continued

| Test 3 Control (1–9) | | | | % Control | | | | Treatment | Crabgrass | | Dandelion | | Clover | | Plantain | |
|---|---|---|---|---|---|---|---|---|---|---|---|---|---|---|---|---|
| Crab-grass | Dan-de-lion | Clo-ver | Plan-tain | Crab-grass | Dan-de-lion | Clo-ver | Plan-tain | | Ex-pected | Actual | Ex-pected | Actual | Ex-pected | Actual | Ex-pected | Actual |
| 7 | 6 | 4 | 8 | 77.8 | 66.7 | 44.4 | 88.9 | 0.75 Quinclorac + 0.02 Sulfentrazone | 56.8 | 77.8 | 56.8 | 66.7 | 63.0 | 44.4 | 100.0 | 88.9 |
| 7 | 7 | 4 | 9 | 77.8 | 77.8 | 44.4 | 100.0 | 0.375 Quinclorac + 0.03 Sulfentrazone | 65.4 | 77.8 | 74.1 | 77.8 | 69.1 | 44.4 | 92.6 | 100.0 |
| 6 | 7 | 4 | 8 | 66.7 | 77.8 | 44.4 | 88.9 | 0.375 Quinclorac + 0.02 Sulfentrazone | 56.8 | 66.7 | 56.8 | 77.8 | 63.0 | 44.4 | 100.0 | 88.9 |
| 6 | 6 | 4 | 9 | 66.7 | 66.7 | 44.4 | 100.0 | 0.18 Quinclorac + 0.03 Sulfentrazone | 65.4 | 66.7 | 74.1 | 66.7 | 69.1 | 44.4 | 91.4 | 100.0 |
| 6 | 6 | 4 | 8 | 66.7 | 66.7 | 44.4 | 88.9 | 0.18 Quinclorac + 0.02 Sulfentrazone | 56.8 | 66.7 | 56.8 | 66.7 | 63.0 | 44.4 | 100.0 | 88.9 |
| 8 | 8 | 8 | 9 | 88.9 | 88.9 | 88.9 | 100.0 | 0.75 Quinclorac + 0.03 Sulfentrazone + 1.10 MCPA IOE | 69.3 | 88.9 | 91.4 | 88.9 | 89.7 | 88.9 | 97.5 | 100.0 |
| 8 | 8 | 8 | 9 | 88.9 | 88.9 | 88.9 | 100.0 | 0.75 Quinclorac + 0.02 Sulfentrazone + 1.10 MCPA IOE | 61.6 | 88.9 | 85.6 | 88.9 | 87.7 | 88.9 | 100.0 | 100.0 |
| 8 | 8 | 8 | 9 | 88.9 | 88.9 | 88.9 | 100.0 | 0.375 Quinclorac + 0.03 Sulfentrazone + 1.10 MCPA IOE | 69.3 | 88.9 | 91.4 | 88.9 | 89.7 | 88.9 | 97.5 | 100.0 |
| 8 | 8 | 8 | 9 | 88.9 | 88.9 | 88.9 | 100.0 | 0.375 Quinclorac + 0.02 Sulfentrazone + 1.10 MCPA IOE | 61.6 | 88.9 | 85.6 | 88.9 | 87.7 | 88.9 | 100.0 | 100.0 |
| 14 DAT | | | | 14 DAT | | | | | | | | | | | | |
| 5 | 4 | 5 | 5 | 66.7 | 44.4 | 55.6 | 55.6 | Quinclorac @ 0.75 lbs/A | | | | | | | | |
| 4 | 4 | 5 | 4 | 44.4 | 44.4 | 55.6 | 44.4 | Quinclorac @ 0.375 lbs/A | | | | | | | | |
| 3 | 3 | 4 | 3 | 33.3 | 33.3 | 44.4 | 33.3 | Quinclorac @ 0.18 lbs/A | | | | | | | | |
| 5 | 7 | 5 | 8 | 55.6 | 77.8 | 55.6 | 88.9 | Sulfentrazone @ 0.03 lbs/A | | | | | | | | |
| 4 | 7 | 4 | 9 | 44.4 | 77.8 | 44.4 | 100.0 | Sulfentrazone @ 0.02 lbs/A | | | | | | | | |
| 2 | 7 | 8 | 7 | 22.2 | 77.8 | 88.9 | 77.8 | MCPA IOE @ 1.10 lbs/A | | | | | | | | |
| 7 | 7 | 5 | 9 | 77.8 | 77.8 | 55.6 | 100.0 | 0.75 Quinclorac + 0.03 Sulfentrazone | 85.2 | 77.8 | 87.7 | 77.8 | 80.2 | 55.6 | 95.1 | 100.0 |
| 7 | 8 | 5 | 8 | 77.8 | 88.9 | 55.6 | 88.9 | 0.75 Quinclorac + 0.02 Sulfentrazone | 81.5 | 77.8 | 87.7 | 88.9 | 75.3 | 55.6 | 100.0 | 88.9 |
| 7 | 8 | 5 | 9 | 77.8 | 88.9 | 55.6 | 100.0 | 0.375 Quinclorac + 0.03 Sulfentrazone | 75.3 | 77.8 | 87.7 | 88.9 | 80.2 | 55.6 | 93.8 | 100.0 |

-continued

| Test 3 Control (1–9) | | | | % Control | | | | Treatment | Crabgrass | | Dandelion | | Clover | | Plantain | |
|---|---|---|---|---|---|---|---|---|---|---|---|---|---|---|---|---|
| Crab-grass | Dan-de-lion | Clo-ver | Plan-tain | Crab-grass | Dan-de-lion | Clo-ver | Plan-tain | | Ex-pected | Actual | Ex-pected | Actual | Ex-pected | Actual | Ex-pected | Actual |
| 7 | 8 | 5 | 9 | 77.8 | 88.9 | 55.6 | 100.0 | 0.375 Quinclorac + 0.02 Sulfentrazone | 69.1 | 77.8 | 87.7 | 88.9 | 75.3 | 55.6 | 100.0 | 100.0 |
| 7 | 8 | 5 | 9 | 77.8 | 88.9 | 55.6 | 100.0 | 0.18 Quinclorac + 0.03 Sulfentrazone | 70.4 | 77.8 | 85.2 | 88.9 | 75.3 | 55.6 | 92.6 | 100.0 |
| 7 | 8 | 5 | 9 | 77.8 | 88.9 | 55.6 | 100.0 | 0.18 Quinclorac + 0.02 Sulfentrazone | 63.0 | 77.8 | 85.2 | 88.9 | 69.1 | 55.6 | 100.0 | 100.0 |
| 8 | 8 | 8 | 9 | 88.9 | 88.9 | 88.9 | 100.0 | 0.75 Quinclorac + 0.03 Sulfentrazone + 1.10 MCPA IOE | 88.5 | 88.9 | 97.3 | 88.9 | 97.8 | 88.9 | 98.9 | 100.0 |
| 8 | 8 | 8 | 9 | 88.9 | 88.9 | 88.9 | 100.0 | 0.75 Quinclorac + 0.02 Sulfentrazone + 1.10 MCPA IOE | 85.6 | 88.9 | 97.3 | 88.9 | 97.3 | 88.9 | 100.0 | 100.0 |
| 8 | 8 | 8 | 9 | 88.9 | 88.9 | 88.9 | 100.0 | 0.375 Quinclorac + 0.03 Sulfentrazone + 1.10 MCPA IOE | 80.8 | 88.9 | 97.3 | 88.9 | 97.8 | 88.9 | 98.6 | 100.0 |
| 8 | 8 | 8 | 9 | 88.9 | 88.9 | 88.9 | 100.0 | 0.375 Quinclorac + 0.02 Sulfentrazone + 1.10 MCPA IOE | 76.0 | 88.9 | 97.3 | 88.9 | 97.3 | 88.9 | 100.0 | 100.0 |
| 21 DAT | | | | 21 DAT | | | | | | | | | | | | |
| 7 | 3 | 8 | 5 | 77.8 | 33.3 | 88.9 | 55.6 | Quinclorac @ 0.75 lbs/A | | | | | | | | |
| 6 | 5 | 8 | 4 | 66.7 | 55.6 | 88.9 | 44.4 | Quinclorac @ 0.375 lbs/A | | | | | | | | |
| 3 | 3 | 6 | 3 | 33.3 | 33.3 | 66.7 | 33.3 | Quinclorac @ 0.18 lbs/A | | | | | | | | |
| 4 | 7 | 5 | 9 | 44.4 | 77.8 | 55.6 | 100.0 | Sulfentrazone @ 0.03 lbs/A | | | | | | | | |
| 3 | 6 | 4 | 9 | 33.3 | 66.7 | 44.4 | 100.0 | Sulfentrazone @ 0.02 lbs/A | | | | | | | | |
| 4 | 8 | 9 | 7 | 44.4 | 88.9 | 100.0 | 77.8 | MCPA IOE @ 1.10 lbs/A | | | | | | | | |
| 7 | 9 | 6 | 9 | 77.8 | 100.0 | 66.7 | 100.0 | 0.75 Quinclorac + 0.03 Sulfentrazone | 87.7 | 77.8 | 85.2 | 100.0 | 95.1 | 66.7 | 100.0 | 100.0 |
| 7 | 9 | 5 | 9 | 77.8 | 100.0 | 55.6 | 100.0 | 0.75 Quinclorac + 0.02 Sulfentrazone | 85.2 | 77.8 | 77.8 | 100.0 | 93.8 | 55.6 | 100.0 | 100.0 |
| 7 | 8 | 7 | 9 | 77.8 | 88.9 | 77.8 | 100.0 | 0.375 Quinclorac + 0.03 Sulfentrazone | 81.5 | 77.8 | 90.1 | 88.9 | 95.1 | 77.8 | 100.0 | 100.0 |
| 7 | 8 | 6 | 9 | 77.8 | 88.9 | 66.7 | 100.0 | 0.375 Quinclorac + 0.02 Sulfentrazone | 77.8 | 77.8 | 85.2 | 88.9 | 93.8 | 66.7 | 100.0 | 100.0 |
| 7 | 8 | 7 | 9 | 77.8 | 88.9 | 77.8 | 100.0 | 0.18 Quinclorac + 0.03 Sulfentrazone | 62.9 | 77.8 | 85.2 | 88.9 | 85.2 | 77.8 | 100.0 | 100.0 |

| Test 3 Control (1–9) | | | | % Control | | | | | Crabgrass | | Dandelion | | Clover | | Plantain | |
|---|---|---|---|---|---|---|---|---|---|---|---|---|---|---|---|---|
| Crab-grass | Dan-de-lion | Clo-ver | Plan-tain | Crab-grass | Dan-de-lion | Clo-ver | Plan-tain | Treatment | Ex-pected | Actual | Ex-pected | Actual | Ex-pected | Actual | Ex-pected | Actual |
| 7 | 8 | 6 | 9 | 77.8 | 88.9 | 66.7 | 100.0 | 0.18 Quinclorac + 0.02 Sulfentrazone | 55.6 | 77.8 | 77.8 | 88.9 | 81.5 | 66.7 | 100.0 | 100.0 |
| 8 | 9 | 9 | 9 | 88.9 | 100.0 | 100.0 | 100.0 | 0.75 Quinclorac + 0.03 Sulfen-trazone + 1.10 MCPA IOE | 93.1 | 88.9 | 98.4 | 100.0 | 100.0 | 100.0 | 100.0 | 100.0 |
| 8 | 8 | 9 | 9 | 88.9 | 88.9 | 100.0 | 100.0 | 0.75 Quinclorac + 0.02 Sulfen-trazone + 1.10 MCPA IOE | 91.8 | 88.9 | 97.5 | 88.9 | 100.0 | 100.0 | 100.0 | 100.0 |
| 8 | 9 | 9 | 9 | 88.9 | 100.0 | 100.0 | 100.0 | 0.375 Quinclorac + 0.03 Sulfen-trazone + 1.10 MCPA IOE | 89.7 | 88.9 | 98.9 | 100.0 | 100.0 | 100.0 | 100.0 | 100.0 |
| 8 | 9 | 9 | 9 | 88.9 | 100.0 | 100.0 | 100.0 | 0.375 Quinclorac + 0.02 Sulfen-trazone + 1.10 MCPA IOE | 87.7 | 88.9 | 98.4 | 100.0 | 100.0 | 100.0 | 100.0 | 100.0 |

| Test 4 Control (1–9) | | | | % Control | | | | | Crabgrass | | Dandelion | | Clover | | Plantain | |
|---|---|---|---|---|---|---|---|---|---|---|---|---|---|---|---|---|
| Crab-grass | Dan-de-lion | Clo-ver | Plan-tain | Crab-grass | Dan-de-lion | Clo-ver | Plan-tain | Treatment | Ex-pected | Actual | Ex-pected | Actual | Ex-pected | Actual | Ex-pected | Actual |
| 24 HAT | | | | 24 HAT | | | | | | | | | | | | |
| 1 | 1 | 1 | 1 | 11.1 | 11.1 | 11.1 | 11.1 | Quinclorac @ 0.75 lbs/A | | | | | | | | |
| 1 | 2 | 1 | 1 | 11.1 | 22.2 | 11.1 | 11.1 | Quinclorac @ 0.375 lbs/A | | | | | | | | |
| 1 | 1 | 1 | 1 | 11.1 | 11.1 | 11.1 | 11.1 | Quinclorac @ 0.18 lbs/A | | | | | | | | |
| 1 | 3 | 4 | 3 | 11.1 | 33.3 | 44.4 | 33.3 | Carfen-trazone @ 0.02 lbs/A | | | | | | | | |
| 1 | 2 | 2 | 3 | 11.1 | 22.2 | 22.2 | 33.3 | Carfen-trazone @ 0.01 lbs/A | | | | | | | | |
| 1 | 3 | 4 | 2 | 11.1 | 33.3 | 44.4 | 22.2 | MCPA IOE @ 1.10 lbs/A | | | | | | | | |
| 1 | 3 | 4 | 4 | 11.1 | 33.3 | 44.4 | 44.4 | 0.75 Quinclorac + 0.02 Carfentrazone | 21.0 | 11.1 | 40.7 | 33.3 | 50.6 | 44.4 | 40.7 | 44.4 |
| 1 | 3 | 3 | 4 | 11.1 | 33.3 | 33.3 | 44.4 | 0.75 Quinclorac + 0.01 Carfentrazone | 21.0 | 11.1 | 30.9 | 33.3 | 30.9 | 33.3 | 40.7 | 44.4 |
| 1 | 3 | 3 | 5 | 11.1 | 33.3 | 33.3 | 55.6 | 0.375 Quinclorac + 0.02 Carfentrazone | 21.0 | 11.1 | 48.1 | 33.3 | 50.6 | 33.3 | 40.7 | 55.6 |

-continued

| Test 4 Control (1–9) | | | | % Control | | | | Treatment | Crabgrass | | Dandelion | | Clover | | Plantain | |
|---|---|---|---|---|---|---|---|---|---|---|---|---|---|---|---|---|
| Crabgrass | Dandelion | Clover | Plantain | Crabgrass | Dandelion | Clover | Plantain | | Expected | Actual | Expected | Actual | Expected | Actual | Expected | Actual |
| 1 | 3 | 3 | 4 | 11.1 | 33.3 | 33.3 | 44.4 | 0.375 Quinclorac + 0.01 Carfentrazone | 21.0 | 11.1 | 39.5 | 33.3 | 30.9 | 33.3 | 40.7 | 44.4 |
| 1 | 3 | 3 | 4 | 11.1 | 33.3 | 33.3 | 44.4 | 0.18 Quinclorac + 0.02 Carfentrazone | 21.0 | 11.1 | 40.7 | 33.3 | 50.6 | 33.3 | 40.7 | 44.4 |
| 1 | 3 | 3 | 5 | 11.1 | 33.3 | 33.3 | 55.6 | 0.18 Quinclorac + 0.01 Carfentrazone | 21.0 | 11.1 | 30.9 | 33.3 | 30.9 | 33.3 | 40.7 | 55.6 |
| 1 | 3 | 5 | 4 | 11.1 | 33.3 | 55.6 | 44.4 | 0.75 Quinclorac + 0.02 Carfentrazone + 1.10 MCPA IOE | 29.8 | 11.1 | 60.5 | 33.3 | 72.6 | 55.6 | 53.9 | 44.4 |
| 1 | 4 | 5 | 5 | 11.1 | 44.4 | 55.6 | 55.6 | 0.75 Quinclorac + 0.01 Carfentrazone + 1.10 MCPA IOE | 29.8 | 11.1 | 53.9 | 44.4 | 61.6 | 55.6 | 53.9 | 55.6 |
| 1 | 4 | 5 | 5 | 11.1 | 44.4 | 55.6 | 55.6 | 0.375 Quinclorac + 0.02 Carfentrazone + 1.10 MCPA IOE | 29.8 | 11.1 | 65.4 | 44.4 | 72.6 | 55.6 | 53.9 | 55.6 |
| 1 | 4 | 5 | 5 | 11.1 | 44.4 | 55.6 | 55.6 | 0.375 Quinclorac + 0.01 Carfentrazone + 1.10 MCPA IOE | 29.8 | 11.1 | 59.7 | 44.4 | 61.6 | 55.6 | 53.9 | 55.6 |
| 72 HAT | | | | 72 HAT | | | | | | | | | | | | |
| 2 | 2 | 2 | 3 | 22.2 | 22.2 | 22.2 | 33.3 | Quinclorac @ 0.75 lbs/A | | | | | | | | |
| 1 | 2 | 2 | 2 | 11.1 | 22.2 | 22.2 | 22.2 | Quinclorac @ 0.375 lbs/A | | | | | | | | |
| 1 | 2 | 2 | 2 | 11.1 | 22.2 | 22.2 | 22.2 | Quinclorac @ 0.18 lbs/A | | | | | | | | |
| 4 | 5 | 4 | 6 | 44.4 | 55.6 | 44.4 | 66.7 | Carfentrazone @ 0.02 lbs/A | | | | | | | | |
| 2 | 3 | 4 | 8 | 22.2 | 33.3 | 44.4 | 88.9 | Carfentrazone @ 0.01 lbs/A | | | | | | | | |
| 1 | 5 | 5 | 4 | 11.1 | 55.6 | 55.6 | 44.4 | MCPA IOE @ 1.10 lbs/A | | | | | | | | |
| 3 | 5 | 5 | 8 | 33.3 | 55.6 | 55.6 | 88.9 | 0.75 Quinclorac + 0.02 Carfentrazone | 56.8 | 33.3 | 65.4 | 55.6 | 56.8 | 55.6 | 77.8 | 88.9 |
| 3 | 5 | 5 | 8 | 33.3 | 55.6 | 55.6 | 88.9 | 0.75 Quinclorac + 0.01 Carfentrazone | 39.5 | 33.3 | 48.1 | 55.6 | 56.8 | 55.6 | 92.6 | 88.9 |
| 5 | 5 | 4 | 8 | 55.6 | 55.6 | 44.4 | 88.9 | 0.375 Quinclorac + 0.02 Carfentrazone | 50.6 | 55.6 | 65.4 | 55.6 | 56.8 | 44.4 | 74.1 | 88.9 |
| 3 | 5 | 4 | 8 | 33.3 | 55.6 | 44.4 | 88.9 | 0.375 Quinclorac + 0.01 Carfentrazone | 30.9 | 33.3 | 48.1 | 55.6 | 56.8 | 44.4 | 91.4 | 88.9 |
| 5 | 5 | 5 | 8 | 55.6 | 55.6 | 55.6 | 88.9 | 0.18 Quinclorac + 0.02 Carfentrazone | 50.6 | 55.6 | 65.4 | 55.6 | 56.8 | 55.6 | 74.1 | 88.9 |

-continued

| Test 4 Control (1–9) | | | | % Control | | | | Treatment | Crabgrass | | Dandelion | | Clover | | Plantain | |
|---|---|---|---|---|---|---|---|---|---|---|---|---|---|---|---|---|
| Crab-grass | Dan-de-lion | Clo-ver | Plan-tain | Crab-grass | Dan-de-lion | Clo-ver | Plan-tain | | Ex-pected | Actual | Ex-pected | Actual | Ex-pected | Actual | Ex-pected | Actual |
| 4 | 6 | 5 | 8 | 44.4 | 66.7 | 55.6 | 88.9 | 0.18 Quinclorac + 0.01 Carfentrazone | 30.9 | 44.4 | 48.1 | 66.7 | 56.8 | 55.6 | 91.4 | 88.9 |
| 6 | 6 | 6 | 8 | 66.7 | 66.7 | 66.7 | 88.9 | 0.75 Quinclorac + 0.02 Carfen-trazone + 1.10 MCPA IOE | 61.6 | 66.7 | 84.6 | 66.7 | 80.8 | 66.7 | 87.7 | 88.9 |
| 5 | 6 | 6 | 8 | 55.6 | 66.7 | 66.7 | 88.9 | 0.75 Quinclorac + 0.01 Carfen-trazone + 1.10 MCPA IOE | 46.2 | 55.6 | 77.0 | 66.7 | 80.8 | 66.7 | 95.9 | 88.9 |
| 6 | 7 | 6 | 8 | 66.7 | 77.8 | 66.7 | 88.9 | 0.375 Quinclorac + 0.02 Carfen-trazone + 1.10 MCPA IOE | 56.1 | 66.7 | 84.6 | 77.8 | 80.8 | 66.7 | 85.6 | 88.9 |
| 5 | 7 | 6 | 8 | 55.6 | 77.8 | 66.7 | 88.9 | 0.375 Quinclorac + 0.01 Carfen-trazone + 1.10 MCPA IOE | 38.5 | 55.6 | 77.0 | 77.8 | 80.8 | 66.7 | 95.2 | 88.9 |
| 7 DAT | | | | 7 DAT | | | | | | | | | | | | |
| 2 | 2 | 3 | 3 | 22.2 | 22.2 | 33.3 | 33.3 | Quinclorac @ 0.75 lbs/A | | | | | | | | |
| 2 | 2 | 4 | 2 | 22.2 | 22.2 | 44.4 | 22.2 | Quinclorac @ 0.375 lbs/A | | | | | | | | |
| 1 | 2 | 3 | 3 | 11.1 | 22.2 | 33.3 | 33.3 | Quinclorac @ 0.18 lbs/A | | | | | | | | |
| 5 | 8 | 7 | 8 | 55.6 | 88.9 | 77.8 | 88.9 | Carfen-trazone @ 0.02 lbs/A | | | | | | | | |
| 5 | 5 | 6 | 9 | 55.6 | 55.6 | 66.7 | 100.0 | Carfen-trazone @ 0.01 lbs/A | | | | | | | | |
| 1 | 4 | 6 | 6 | 11.1 | 44.4 | 66.7 | 66.7 | MCPA IOE @ 1.10 lbs/A | | | | | | | | |
| 6 | 8 | 6 | 9 | 66.7 | 88.9 | 66.7 | 100.0 | 0.75 Quinclorac + 0.02 Carfentrazone | 65.4 | 66.7 | 91.4 | 88.9 | 85.2 | 66.7 | 92.6 | 100.0 |
| 6 | 8 | 6 | 9 | 66.7 | 88.9 | 66.7 | 100.0 | 0.75 Quinclorac + 0.01 Carfentrazone | 65.4 | 66.7 | 65.4 | 88.9 | 77.8 | 66.7 | 100.0 | 100.0 |
| 6 | 8 | 6 | 9 | 66.7 | 88.9 | 66.7 | 100.0 | 0.375 Quinclorac + 0.02 Carfentrazone | 65.5 | 66.7 | 91.4 | 88.9 | 87.7 | 66.7 | 91.4 | 100.0 |
| 5 | 7 | 6 | 8 | 55.6 | 77.8 | 66.7 | 88.9 | 0.375 Quinclorac + 0.01 Carfentrazone | 65.4 | 55.6 | 65.4 | 77.8 | 81.5 | 66.7 | 100.0 | 88.9 |
| 6 | 8 | 6 | 9 | 66.7 | 88.9 | 66.7 | 100.0 | 0.18 Quinclorac + 0.02 Carfentrazone | 60.5 | 66.7 | 91.4 | 88.9 | 85.2 | 66.7 | 92.6 | 100.0 |
| 6 | 8 | 6 | 8 | 66.7 | 88.9 | 66.7 | 88.9 | 0.18 Quinclorac + 0.01 Carfentrazone | 60.5 | 66.7 | 65.4 | 88.9 | 77.8 | 66.7 | 100.0 | 88.9 |

-continued

| Test 4 Control (1–9) | | | | % Control | | | | Treatment | Crabgrass | | Dandelion | | Clover | | Plantain | |
|---|---|---|---|---|---|---|---|---|---|---|---|---|---|---|---|---|
| Crab-grass | Dan-de-lion | Clo-ver | Plan-tain | Crab-grass | Dan-de-lion | Clo-ver | Plan-tain | | Ex-pected | Actual | Ex-pected | Actual | Ex-pected | Actual | Ex-pected | Actual |
| 8 | 8 | 9 | 9 | 88.9 | 88.9 | 100.0 | 100.0 | 0.75 Quinclorac + 0.02 Carfen-trazone + 1.10 MCPA IOE | 69.3 | 77.8 | 95.2 | 88.9 | 95.1 | 100.0 | 97.5 | 100.0 |
| 7 | 8 | 9 | 8 | 77.8 | 88.9 | 100.0 | 88.9 | 0.75 Quinclorac + 0.01 Carfen-trazone + 1.10 MCPA IOE | 69.3 | 77.8 | 80.8 | 88.9 | 92.6 | 100.0 | 100.0 | 88.9 |
| 7 | 9 | 9 | 9 | 77.8 | 100.0 | 100.0 | 100.0 | 0.375 Quinclorac + 0.02 Carfen-trazone + 1.10 MCPA IOE | 69.3 | 77.8 | 95.2 | 100.0 | 95.9 | 100.0 | 97.1 | 100.0 |
| 7 | 8 | 9 | 9 | 77.8 | 88.9 | 100.0 | 100.0 | 0.375 Quinclorac + 0.01 Carfen-trazone + 1.10 MCPA IOE | 69.3 | 77.8 | 80.8 | 88.9 | 93.8 | 100.0 | 100.0 | 100.0 |
| 14 DAT | | | | 14 DAT | | | | | | | | | | | | |
| 5 | 2 | 4 | 3 | 44.4 | 22.2 | 44.4 | 33.3 | Quinclorac @ 0.75 lbs/A | | | | | | | | |
| 3 | 2 | 5 | 2 | 33.3 | 22.2 | 55.6 | 22.2 | Quinclorac @ 0.375 lbs/A | | | | | | | | |
| 2 | 2 | 3 | 3 | 22.2 | 22.2 | 33.3 | 33.3 | Quinclorac @ 0.18 lbs/A | | | | | | | | |
| 5 | 8 | 8 | 8 | 55.6 | 88.9 | 88.9 | 88.9 | Carfen-trazone @ 0.02 lbs/A | | | | | | | | |
| 5 | 5 | 6 | 9 | 55.6 | 55.6 | 66.7 | 100.0 | Carfen-trazone @ 0.01 lbs/A | | | | | | | | |
| 1 | 5 | 9 | 6 | 11.1 | 55.6 | 100.0 | 66.7 | MCPA IOE @ 1.10 lbs/A | | | | | | | | |
| 7 | 9 | 8 | 9 | 77.8 | 100.0 | 88.9 | 100.0 | 0.75 Quinclorac + 0.02 Carfentrazone | 75.3 | 77.8 | 91.4 | 100.0 | 93.8 | 88.9 | 92.6 | 100.0 |
| 8 | 8 | 7 | 9 | 88.9 | 88.9 | 77.8 | 100.0 | 0.75 Quinclorac + 0.01 Carfentrazone | 75.3 | 88.9 | 65.4 | 88.9 | 81.5 | 77.8 | 100.0 | 100.0 |
| 8 | 8 | 7 | 9 | 88.9 | 88.9 | 77.8 | 100.0 | 0.375 Quinclorac + 0.02 Carfentrazone | 70.4 | 88.9 | 91.4 | 88.9 | 95.1 | 77.8 | 91.4 | 100.0 |
| 7 | 8 | 7 | 9 | 77.8 | 88.9 | 77.8 | 100.0 | 0.375 Quinclorac + 0.01 Carfentrazone | 70.4 | 77.8 | 65.4 | 88.9 | 85.2 | 77.8 | 100.0 | 100.0 |
| 7 | 8 | 7 | 9 | 77.8 | 88.9 | 77.8 | 100.0 | 0.18 Quinclorac + 0.02 Carfentrazone | 65.5 | 77.8 | 91.4 | 88.9 | 92.6 | 77.8 | 92.6 | 100.0 |
| 7 | 8 | 7 | 9 | 77.8 | 88.9 | 77.8 | 100.0 | 0.18 Quinclorac + 0.01 Carfentrazone | 65.4 | 77.8 | 65.4 | 88.9 | 77.8 | 77.8 | 100.0 | 100.0 |
| 8 | 9 | 9 | 9 | 88.9 | 100.0 | 100.0 | 100.0 | 0.75 Quinclorac + 0.02 Carfen-trazone + 1.10 MCPA IOE | 78.1 | 88.9 | 96.2 | 100.0 | 100.0 | 100.0 | 97.5 | 100.0 |

-continued

| Test 4 Control (1–9) | | | | % Control | | | | | Crabgrass | | Dandelion | | Clover | | Plantain | |
|---|---|---|---|---|---|---|---|---|---|---|---|---|---|---|---|---|
| Crab-grass | Dan-de-lion | Clo-ver | Plan-tain | Crab-grass | Dan-de-lion | Clo-ver | Plan-tain | Treatment | Ex-pected | Actual | Ex-pected | Actual | Ex-pected | Actual | Ex-pected | Actual |
| 8 | 9 | 9 | 9 | 88.9 | 100.0 | 100.0 | 100.0 | 0.75 Quinclorac + 0.01 Carfen-trazone + 1.10 MCPA IOE | 78.0 | 88.9 | 84.6 | 100.0 | 100.0 | 100.0 | 100.0 | 100.0 |
| 8 | 9 | 9 | 9 | 88.9 | 100.0 | 100.0 | 100.0 | 0.375 Quinclorac + 0.02 Carfen-trazone + 1.10 MCPA IOE | 73.7 | 88.9 | 96.2 | 100.0 | 100.0 | 100.0 | 97.1 | 100.0 |
| 8 | 9 | 9 | 9 | 88.9 | 100.0 | 100.0 | 100.0 | 0.375 Quinclorac + 0.01 Carfen-trazone + 1.10 MCPA IOE | 73.7 | 88.9 | 84.6 | 100.0 | 100.0 | 100.0 | 100.0 | 100.0 |

What is claimed is:

1. A selective synergistic postemergent herbicidal composition for the control of undesired vegetation when applied at a recommended application rate to the locus of the undesired vegetation, said composition comprising as herbicidally active ingredients:
   quinclorac herbicide;
   a selective herbicidal protox inhibitor; and
   a selective herbicidal auxinic agent,
   said composition when applied for undesired vegetation control containing sufficient amounts of the quinclorac, the protox inhibitor and the auxinic agent to supply from about 0.1 to about 1 lb/acre of quinclorac, from about 0.005 to about 0.06 lb/acre of the protox inhibitor, and from about 0.15 to about 2 lbs/acre of the auxinic agent.

2. A herbicidal composition as set forth in claim 1, wherein the composition as applied for undesired vegetation control contains an amount of quinclorac sufficient to supply from about 0.18 to about 0.75 lb/acre of quinclorac.

3. A herbicidal composition as set forth in claim 1, wherein the composition as applied for undesired vegetation control contains an amount of said quinclorac agent sufficient to supply about 0.375 lb/acre of quinclorac.

4. A herbicidal composition as set forth in claim 1, wherein the composition as applied for undesired vegetation control contains an amount of the protox inhibitor sufficient to supply from about 0.01 to about 0.05 lb/acre of the protox inhibitor.

5. A herbicidal composition as set forth in claim 1, wherein the composition as applied for undesired vegetation control contains an amount of the protox inhibitor sufficient to supply from about 0.02 to about 0.03 lb/acre of the protox inhibitor.

6. A herbicidal composition as set forth in claim 1, wherein the composition as applied for undesired vegetation control contains an amount of the auxinic agent sufficient to supply from about 0.25 to about 1.5 lb/acre of said auxinic agent.

7. A herbicidal composition as set forth in claim 1, wherein the composition as applied for undesired vegetation control contains an amount of the auxinic agent sufficient to supply about 0.75 lb/acre of the auxinic agent.

8. A herbicidal composition as set forth in claim 1, wherein the protox inhibitor is selected from the group consisting of carfentrazone-ethyl, sulfentrazone, pyraflufen-ethyl, flumioxazin, fluthiacet-methyl and oxyfluorfen.

9. A herbicidal composition as set forth in claim 1, wherein the protox inhibitor is carfentrazone-ethyl.

10. A herbicidal composition as set forth in claim 1, wherein the protox inhibitor is sulfentrazone.

11. A herbicidal composition as set forth in claim 1, wherein the protox inhibitor is pyraflufen-ethyl.

12. A herbicidal composition as set forth in claim 1, wherein the auxinic herbicidal agent is selected from the group consisting of herbicidally active phenoxy, benzoic, pyridine, quinolinecarboxylic acid compounds, other than quinclorac, and esters and amine and inorganic salts thereof.

13. A selective synergistic postemergent herbicidal composition for the control of undesired vegetation when applied at a recommended application rate to the locus of the undesired vegetation, said composition comprising as herbicidally active ingredients:
   quinclorac herbicide; and
   a selective protox herbicidal inhibitor,
   said composition when applied for undesired vegetation control containing sufficient amounts of said quinclorac and the protox inhibitor to supply from about 0.1 to about 1 lb/acre of quinclorac and from about 0.005 to about 0.06 lb/acre of the protox herbicidal inhibitor.

14. A herbicidal composition as set forth in claim 13, wherein the composition as applied for undesired vegetation control contains an amount of quinclorac sufficient to supply from about 0.18 to about 0.75 lb/acre of quinclorac.

15. A herbicidal composition as set forth in claim 13, wherein the composition as applied for undesired vegetation control contains an amount of quinclorac sufficient to supply about 0.375 lb/acre of quinclorac.

16. A herbicidal composition as set forth in claim 13, wherein the composition as applied for undesired vegetation control contains an amount of the protox inhibitor sufficient to supply from about 0.01 to about 0.05 lb/acre of the protox inhibitor.

17. A herbicidal composition as set forth in claim 13, wherein the composition as applied for undesired vegetation control contains an amount of the protox inhibitor sufficient to supply from about 0.02 to about 0.03 lb/acre of the protox inhibitor.

18. A herbicidal composition as set forth in claim 13, wherein the protox inhibitor is selected from the group consisting of carfentrazone-ethyl, sulfentrazone, pyraflufen-ethyl, flumioxazin, fluthiacet-methyl and oxyfluorfen.

19. A herbicidal composition as set forth in claim 13, wherein the protox inhibitor is carfentrazone-ethyl.

20. A herbicidal composition as set forth in claim 13, wherein the protox inhibitor is sulfentrazone.

21. A herbicidal composition as set forth in claim 13, wherein the protox inhibitor is pyraflufen-ethyl.

22. A herbicidal composition as set forth in claim 13, wherein the composition contains water and/or an organic-based solvent for herbicidally active ingredients.

23. A method of controlling undesired vegetation when applied at a recommended application rate to the locus of the undesired vegetation, said method comprising:

applying to the locus of the undesired vegetation, a herbicidally effective amount of a composition comprising as herbicidally active postemergent herbicidal ingredients, quinclorac, a selective herbicidal protox inhibitor, and a selective auxinic herbicidal agent, the composition containing the agent and the inhibitor being applied at a rate sufficient to supply from about 0.1 to about 1 lb/acre of the quinclorac, from about 0.005 to about 0.06 lb/acre of the protox inhibitor and from about 0.15 to about 2 lbs/acre of the auxinic agent.

24. The method of claim 23, wherein the composition is applied to the locus of the undesired vegetation at a rate sufficient to supply from about 0.18 to about 0.75 lb/acre of quinclorac.

25. The method of claim 23, wherein the composition is applied to the locus of the undesired vegetation at a rate sufficient to supply about 0.375 lb/acre of quinclorac.

26. The method of claim 23, wherein the composition is applied to the locus of the undesired vegetation at a rate sufficient to supply from about 0.01 to about 0.05 lb/acre of the protox inhibitor.

27. The method of claim 23, wherein the composition is applied to the locus of the undesired vegetation at a rate sufficient to supply from about 0.02 to about 0.03 lb/acre of the protox inhibitor.

28. The method of claim 23, wherein the composition is applied to the locus of the undesired vegetation at a rate sufficient to supply from about 0.25 to about 1.5 lb/acre of the auxinic agent.

29. The method of claim 23, wherein the composition is applied to the locus of the undesired vegetation at a rate sufficient to supply about 0.75 lb/acre of said auxinic agent.

30. The method of claim 23, wherein the protox inhibitor is selected from the group consisting of carfentrazone-ethyl, sulfentrazone, pyraflufen-ethyl, flumioxazin, fluthiacet-methyl and oxyfluorfen.

31. The method of claim 23, wherein the protox inhibitor applied to the locus of the undesired vegetation is carfentrazone-ethyl.

32. The method of claim 23, wherein protox inhibitor applied to the locus of the undesired vegetation is sulfentrazone.

33. The method of claim 23, wherein protox inhibitor applied to the locus of the undesired vegetation is pyraflufen-ethyl.

34. The method of claim 23, wherein the auxinic herbicidal agent applied to the locus of the undesired vegetation is selected from the group consisting of herbicidally active phenoxy, benzoic, pyridine, quinolinecarboxylic acid compounds, other than quinclorac, and esters and amine and inorganic salts thereof.

35. A method of controlling undesired vegetation, said method comprising:

applying to the locus of the vegetation, a herbicidally effective amount of a composition comprising as herbicidally active ingredients, quinclorac herbicide and a selective herbicidal protox inhibitor, the composition containing the agent and the inhibitor being applied at a rate sufficient to supply from about 0.1 to about 1 lb/acre of the quinclorac and from about 0.005 to about 0.06 lb/acre of the protox inhibitor.

36. The method of claim 35, wherein the composition is applied to the locus of the undesired vegetation at a rate sufficient to supply from about 0.18 to about 0.75 lb/acre of said quinclorac.

37. The method of claim 35, wherein the composition is applied to the locus of the undesired vegetation at a rate sufficient to supply about 0.375 lb/acre of said quinclorac.

38. The method of claim 35, wherein the composition is applied to the locus of the undesired vegetation at a rate sufficient to supply from about 0.01 to about 0.03 lb/acre of the protox inhibitor.

39. The method of claim 35, wherein the composition is applied to the locus of the undesired vegetation at a rate sufficient to supply from about 0.2 to about 0.3 lb/acre of the protox inhibitor.

40. The method of claim 35, wherein the protox inhibitor is selected from the group consisting of carfentrazone-ethyl, sulfentrazone, pyraflufen-ethyl, flumioxazin, fluthiacet-methyl and oxyfluorfen.

41. The method of claim 35, wherein the protox inhibitor applied to the locus of the undesired vegetation is carfentrazone-ethyl.

42. The method of claim 35, wherein protox inhibitor applied to the locus of the undesired vegetation is sulfentrazone.

43. The method of claim 35, wherein protox inhibitor applied to the locus of the vegetation is pyraflufen-ethyl.

44. A selective synergistic postemergent herbicidal composition for the control of undesired vegetation when applied to the locus of the undesired vegetation, said composition comprising:

herbicidally effective amounts of the synergistic combination of quinclorac, a herbicidal protox inhibitor, and a herbicidal auxinic compound.

45. A herbicidal composition as set forth in claim 44, wherein the protox inhibitor is selected from the group consisting of carfentrazone-ethyl, sulfentrazone, pyraflufen-ethyl, flumioxazin, fluthiacet-methyl and oxyfluorfen.

46. A herbicidal composition as set forth in claim 44, wherein the protox inhibitor is carfentrazone-ethyl.

47. A herbicidal composition as set forth in claim 44, wherein the protox inhibitor is sulfentrazone.

48. A herbicidal composition as set forth in claim 44, wherein the protox inhibitor is pyraflufen-ethyl.

49. A herbicidal composition as set forth in claim 44, wherein the auxinic herbicidal compound is selected from the group consisting of herbicidally active phenoxy, benzoic, pyridine, quinolinecarboxylic acid compounds, other than quinclorac, and ester and amine and inorganic salts thereof.

50. A selective synergistic postemergent herbicidal composition for the control of undesired vegetation when applied to the locus of the vegetation, said composition comprising:

herbicidally effective amounts of the synergistic combination of quinclorac and a herbicidal protox inhibitor.

51. A herbicidal composition as set forth in claim 50, wherein the protox inhibitor is carfentrazone-ethyl.

52. A herbicidal composition as set forth in claim 50, wherein the protox inhibitor is sulfentrazone.

53. A herbicidal composition as set forth in claim 50, wherein the protox inhibitor is pyraflufen-ethyl.

54. A selective synergistic postemergent herbicidal composition for the control of undesired vegetation when applied at a recommended application rate to the locus of the undesired vegetation, said composition comprising as herbicidally active ingredients:

quinclorac herbicide; and a selective herbicidal protox inhibitor;

said composition containing about 0.05 part to about 0.1 part by weight of protox inhibitor for each part by weight of quinclorac.

55. A herbicidal composition as set forth in claim 54, wherein is provided about 0.08 part by weight of protox inhibitor for each part by weight of quinclorac.

56. A selective synergistic postemergent herbicidal composition for the control of undesired vegetation when applied at a recommended application rate to the locus of the undesired vegetation, said composition comprising as herbicidally active ingredients:

quinclorac herbicide;

a selective herbicidal protox inhibitor; and a selective herbicidal auxinic agent, said composition containing about 0.05 part to about 0.1 part by weight of protox inhibitor for each part by weight of quinclorac, and about 1 to 4 parts by weight of auxinic agent for each part by weight of quinclorac.

57. A herbicidal composition as set forth in claim 56, wherein is provided about 0.08 part by weight of protox inhibitor for each part by weight of quinclorac.

58. A herbicidal composition as set forth in claim 56, wherein is provided about 2 parts by weight of auxinic agent for each part by weight of quinclorac.

* * * * *